United States Patent
Kulkarni et al.

(10) Patent No.: US 7,119,234 B2
(45) Date of Patent: Oct. 10, 2006

(54) PROCESS FOR THE PREPARATION OF 1-(4-CHLOROPHENYL)-4,4-DIMETHYLPENT-1-ENE-3-ONE

(75) Inventors: Shekhar V. Kulkarni, Overland Park, KS (US); Joe J. Hanson, Holt, MO (US)

(73) Assignee: Bayer Cropscience LP, Research Triangle Park, NC (US)

(*) Notice: Subject to any disclaimer, the term of this patent is extended or adjusted under 35 U.S.C. 154(b) by 0 days.

(21) Appl. No.: 10/993,639

(22) Filed: Nov. 19, 2004

(65) Prior Publication Data

US 2006/0111592 A1    May 25, 2006

(51) Int. Cl.
*C07C 45/72* (2006.01)
(52) U.S. Cl. ...................... 568/313; 568/316
(58) Field of Classification Search ............. 568/313, 568/316
See application file for complete search history.

(56) References Cited

U.S. PATENT DOCUMENTS 4,010,204 A * 3/1977 Koster et al. ............... 568/313
6,417,406 B1 * 7/2002 Krill et al. .................. 568/388
6,960,964 B1 * 11/2005 Matsuo et al. ........... 331/117 R

FOREIGN PATENT DOCUMENTS

| DE | 39 21 167 C1 | 10/1990 |
| DE | 40 04 031 C1 | 10/1990 |
| FR | 2 253 505 | 7/1975 |

OTHER PUBLICATIONS

Polish Journal of Chemistry, vol. 56, month unavailable, 1982, Issue 10-12, pp. 1435-1445 Angel Garcia-Raso et al, "Activated Ba(OH)$_2$ as Catalyst in Organic Synthesis".

* cited by examiner

*Primary Examiner*—Sikarl A. Witherspoon
(74) *Attorney, Agent, or Firm*—Richard E. L. Henderson; Raymond J. Harmuth

(57) ABSTRACT

The present invention relates to a method for the preparation of as 1-(4-Chlorophenyl)-4,4-dimethylpent-1-ene-3-one, also known as Phenyl aldol. The process of the present invention utilizes catalysts. The process enables the manufacture of the Phenyl aldol in the absence of a solvent and without crystallization or filtration steps. Yields in the range of about greater than 95% with purities in the range of about greater than 95% have been obtained with the present invention.

29 Claims, 1 Drawing Sheet

PROCESS FOR THE PREPARATION OF 1-(4-CHLOROPHENYL)-4,4-DIMETHYLPENT-1-ENE-3-ONE

BACKGROUND OF THE INVENTION

1. Field of the Invention

The present invention relates to a novel process for the preparation of 1-(4-Chlorophenyl)-4,4-dimethylpent-1-ene-3-one, also known as Phenyl aldol.

2. Description of the Related Art Including Information Disclosed Under 37 CFR 1.97 and 1.98

Phenyl aldol is an important intermediate used in the preparation of agrochemicals.

Phenyl aldol has been manufactured by using solvents in its preparation. Its manufacture is described for example, in German Patents DE 392 11 67 and DE 400 40 31. Phenyl aldol is also described in French Patent No. 2,253,505 and in an article entitled Activated Barium Hydroxide As A Catalyst In Organic Synthesis, Garcia-Raso, et. al., Polish Journal of Chemistry, 1982, Vol. 56, 10–12, pp. 1435–45 (1982). French Patent No. 2,253,505 not only requires filtration and recrystallization steps, but its yields are only about 40 to 80%.

The use of a solvent in the manufacturing process of Phenyl aldol requires a separate storage tank for the solvent and all the associated complications of handling an additional component in the manufacturing sequence. Moreover, known processes for manufacturing Phenyl aldol require additional process steps, including but not limited to crystallization and filtration, which require specialized equipment and additional cycle time to conduct these operations. Also, during those steps, some product loss usually happens.

There is a need in the art for a process for the manufacture of Phenyl aldol which does not require the use of a separate solvent and which can be conducted without additional process steps such as crystallization and filtration.

BRIEF SUMMARY OF THE INVENTION

The present invention relates to a method for the preparation of Phenyl aldol.

The process of the present invention utilizes catalysts. The process enables the manufacture of the Phenyl aldol in the absence of a solvent. The process also avoids the need for crystallization and filtration steps. Yields in the range of about greater than 95% with purities in the range of about greater than 95% have been obtained with the present invention.

Generally, the novel process of the present invention involves reacting p-chlorobenzaldehyde with pinacolone in the presence of a base and a catalytic amount of a phase transfer catalyst with a resulting formation of a two phase (organic phase/aqueous phase) system. The pinacolone may optionally be used in stoichometric excess of that necessary to react with the p-chlorobenzaldehyde. The two phase system may optionally be neutralized with an acid. Before or after removal of the aqueous phase, excess pinacolone, if excess was used, is recovered, optionally for reuse, from the organic phase by distillation, whereupon Phenyl aldol is obtained as the organic phase without the need for crystallization or filtration.

In one embodiment, the present invention involves reacting p-chlorobenzaldehyde with excess pinacolone in the presence of aqueous sodium hydroxide as the base and a catalytic amount of the phase transfer catalyst methyltributylammonium chloride. After optional neutralization of the resultant two phase (organic phase/aqueous phase) system with hydrochloric acid, the aqueous phase (the lower phase) is removed. Excess pinacolone is recovered, optionally for reuse, from the remaining organic phase by distillation, whereupon Phenyl aldol is obtained as the organic phase in yields in the range of about greater than 95% with purities in the range of about greater than 95%, without the need for crystallization or filtration.

DETAILED DESCRIPTION OF THE INVENTION

Figure 1:
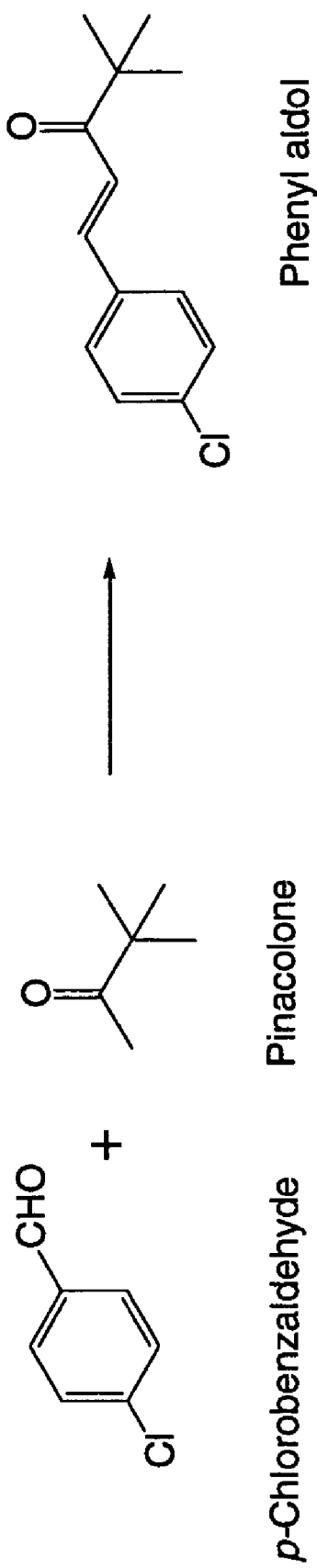
FIG. 1 is a chemical equation illustrating the reaction scheme of producing Phenyl aldol in accordance with the present invention.

As noted above, the present invention relates to a novel process for the preparation of Phenyl aldol.

Generally, the novel process of the present invention involves reacting p-chlorobenzaldehyde with pinacolone in the presence of a base and catalytic amounts of a phase transfer catalyst. As noted above, the pinacolone may optionally be used in stoichometric excess of that necessary to react with the p-chlorobenzaldehyde. Also as noted above, the novel process of the present invention avoids the use of a solvent in the reaction, which avoids the necessity of handling a solvent and the attendant problems (e.g., a separate storage tank for a separate solvent) normally associated with the use of a solvent in a reaction. Additionally and importantly, no crystallization or filtration is necessary with the process of the present invention to obtain the Phenyl aldol. An additional benefit of the present invention is that while the reaction can take place in a wide temperature range, for example any temperature from about 0° C. to the reflux temperature of the reaction mixture. It can preferably proceed in the lower end of that range, preferably in a temperature range of about 30° C. to about 80° C. and still more preferably in the range of about 40° C. to about 60° C.

In one embodiment, the present invention involves reacting p-chlorobenzaldehyde with excess pinacolone in the presence of aqueous sodium hydroxide as the base and a catalytic amount of the phase transfer catalyst methyltributylammonium chloride. After optional neutralization of the resultant two phase (organic phase/aqueous phase) system with hydrochloric acid, separation of the aqueous phase and recovery of excess pinacolone from the organic phase by distillation, Phenyl aldol is obtained as the organic phase in yields in the range of about greater than 95% with purities in the range of about greater than 95%, without the need for crystallization or filtration.

The process of the present invention utilizes phase transfer catalysts. The process of the present invention also enables the manufacture of the Phenyl aldol in the absence of a solvent. The present inventors have found that a catalytic amount of a phase transfer catalyst is important for this procedure, because reactions carried out in the absence of these catalysts under otherwise identical or nearly identical conditions led to poor conversions, selectivity and/or yield. With the catalysts, yields in the range of about greater than 95% with purities in the range of about greater than 95% have been obtained with the process of the present invention.

The ratio of moles of pinacolone to p-chlorobenzaldehyde may be in the range of about 0.5 moles of pinacolone for each mole of p-chlorobenzaldehyde, to about 10 moles of pinacolone for each mole of p-chlorobenzaldehyde. A preferred ratio is in the range of about 1.5 moles of pinacolone for each mole of p-chlorobenzaldehyde to about 5 moles of pinacolone for each mole of p-chlorobenzaldehyde. A particularly preferred ratio is in the range of about 1.75 to about 2.25 moles of pinacolone for each mole of p-chlorobenzaldehyde to get good throughput rates of the product while maintaining good purity and yield of the product.

In general any base containing at least one hydroxide group may be employed within the scope of the present invention. Bases suitable for use in the present invention include alkali metal hydroxides, alkaline earth metal hydroxides and tetraalkylammonium hydroxides. A preferred base is sodium hydroxide. The base is preferably employed in ratio of moles of hydroxide to that of the aldehyde in the range of between about 0.05 to 5.0 moles of hydroxide for each mole of aldehyde, more preferably between about 0.1 to 1 mole of hydroxide for each mole of aldehyde, and still more preferably between about 0.15 to about 0.25 moles of hydroxide per mole of aldehyde, particularly where the base is sodium hydroxide.

The initial concentration of base (such as sodium hydroxide) can also be defined as a percentage. The calculation of this percentage is the weight of base divided by the sum of the weight of base plus the weight of water from all sources. Water can come into the reaction mixture from various sources such as: 1) water present in the aqueous solution of the base; 2) water present in an aqueous solution of the catalyst; 3) water present in the wet reactants (i.e. p-chlorobenzaldehyde and/or pinacolone) and/or 4) water that is added (if it is added) as a separate additive at the beginning of the reaction. For the purpose of this definition the water that is formed in the reaction as a result of the progress of the reaction during the addition of the base is neglected. Under this definition, initial concentration of base in the aqueous phase of the reaction mixture can be between 5% to 80%, preferably between 20% to 50% and most preferably between 30 to 40%.

In general, any suitable phase transfer catalyst may be employed within the scope of the present invention. Phase transfer catalysts compatible with the process of the present invention include tetrasubstituted ammonium halides, tetrasubstituted phosphonium halides and combinations thereof. In particular, tetrabutylammonium bromide, methyltributylammonium chloride, benzyltriethylammonium chloride and/or tetrabutylammonium chloride may be employed within the scope of the present invention. The phase transfer catalyst is employed in a molar ratio of about 0.0001 moles to 1.0 mole of phase transfer catalyst per mole of the aldehyde, preferably about 0.001 moles to 0.1 moles of phase transfer catalyst per mole of the aldehyde.

When the optional neutralization step is employed, any acid which provides the desired neutralization may be employed within the scope of the present invention. Preferred acids are mineral acids, and still more preferred acids are hydrochloric acid, sulfuric acid and/or orthophosphoric acid. The acid is employed in sufficient quantity to bring the pH of the reaction to within the range of about 7 to about 10.

The reaction can also be carried out under reduced or elevated pressures.

The temperature range for the reaction may be in the range of about 0° C. to the reflux temperature of the mixture. However, it can preferably proceed in the lower end of that range, preferably in a temperature range of about 30° C. to about 80° C. and still more preferably in the range of about 40° C. to about 60° C.

After reacting the p-chlorobenzaldehyde, pinacolone, base and phase transfer catalyst to form a reaction mixture, the reaction mixture is optionally neutralized with an aqueous solution of a mineral acid such as concentrated aqueous hydrochloric acid under pH control to neutralize the base present in the aqueous phase of the reaction mixture. The addition of acid is carried out until a pH of about 7 to 10 is reached.

In one variation, this reaction mixture containing both the organic and aqueous phases is then subjected to steam distillation to recover the pinacolone, if the pinacolone was used in excess, and then the agitation is stopped to allow the phases to settle. The lower (aqueous) phase is discarded and the upper (organic) phase which is the product Phenyl aldol is collected.

In another variation, after the optional neutralization is complete, the agitation is stopped and the phases are allowed to separate. The bottom (aqueous) phase is separated and discarded while the organic (upper) phase which contains the excess pinacolone, if the pinacolone was used in excess, is subjected to distillation to recover the excess pinacolone. The residue in the reactor is the product Phenyl aldol. Depending upon the reaction conditions, Phenyl aldol may be obtained in greater than 95% yield (based on p-chlorobenzaldehyde) and in greater than 95% purity.

Since it melts at 85–86° C., it can be pumped into another reactor for further transformation or to a railcar for transport as a liquid if the temperature is maintained above its melting point.

Specific embodiments of the present invention are illustrated in the following examples.

EXAMPLES

Example 1

Pinacolone (400.0 g, 94% pure, 3.76 moles), NaOH (40.0 g, 40 wt % in water, 0.40 moles), tetrabutylammonium bromide (6.0 g, 98% pure, 0.018 moles) and water (2.0 g) were charged into a 2 liter oil-jacketed cylindrical reactor fitted with a mechanical stirrer, thermometer, steam-jacketed addition funnel and a reflux condenser. The reactants were heated to 50° C. and then melted p-chlorobenzaldehyde (280.0 g, 98% pure, 1.95 moles) was added to the reaction mixture via the addition funnel uniformly over 30 minutes. After the addition of the aldehyde was complete, the temperature of the reaction mixture was raised to 60° C. and heated at that temperature for 4 hours. Analysis of the reaction mixture by LC (after neglecting the pinacolone and a small amount of p-chlorobenzoic acid formed by air oxidation of the p-chlorobenzaldehyde) indicated that the organic phase contained 96.2% Phenyl aldol and 0.2% unreacted p-chlorobenzaldehyde. The reaction mixture was then neutralized with 50% aqueous sulfuric acid to pH 8.79 and subjected to steam distillation with the oil temperature in the jacket set to 120° C. to recover all the excess pinacolone. The phases were allowed to settle and the lower (aqueous) phase was discarded. The upper (organic) phase was collected as the product Phenyl aldol.

Example 2

In a 100 gallon stainless steel reactor was charged pinacolone (154.5 kg, 94% pure, 1453 moles), methyltributylammonium chloride (1.09 kg, 75% aqueous solution, 3.47 moles) and water (2.23 kg) and the reactor contents were heated to 40° C. Melted p-chlorobenzaldehyde (109.1 kg, 97.5% pure, 757.1 moles) addition was then started at a rate of 1.82 kg/min (the complete addition therefore took 60 minutes). Ten minutes after the start of the addition of the aldehyde, NaOH (12.36 kg, 50 wt % aqueous solution, 154.5 moles) addition was started at a rate of 0.41 kg/min (the complete addition therefore took 30 minutes). After the addition of the aldehyde was complete, the reactor temperature was increased to 60° C. and heated at that temperature for 3 hours. At that point analysis of the reaction mixture by LC (after negecting the pinacolone and a small amount of p-chlorobenzoic acid formed by air oxidation of the p-chlorobenzaldehyde) indicated that the organic phase contained 96.3% Phenyl aldol and 0.3% unreacted p-chlorobenzaldehyde. The reaction mixture was neutralized with 36% aqueous hydrochloric acid till pH 8.0 and the phases were allowed to settle. The aqueous (lower) phase was discarded and the organic phase was subjected to distillation under reduced pressure to recover all the excess pinacolone. The residue (166.1 kg) was the product Phenyl aldol and was found to be 96.8% pure which translates to a yield of 95.4% based on p-chlorobenzaldehyde.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of Phenyl aldol comprising:
    (a) reacting pinacolone and p-chlorobenzaldehyde in the presence of a base and a phase transfer catalyst to form a reaction mixture comprising an organic phase and an aqueous phase;
    (b) isolating Phenyl aldol from said reaction mixture.

2. The process of claim 1 further optionally comprising neutralizing said reaction mixture.

3. The process of claim 1 wherein said reaction temperature is in the range of about 0° C. to the reflux temperature of said reaction mixture.

4. The process of claim 3 wherein said reaction temperature is in the range of about 30° C. to about 80° C.

5. The process of claim 4 wherein said reaction temperature is in the range of about 40° C. to about 60° C.

6. The process of claim 1 wherein the molar ratio of said pinacolone to said p-chlorobenzaldehyde is between about 0.5 moles of said pinacolone for each mole of said p-chlorobenzaldehyde to about 10 moles of said pinacolone for each mole of said p-chlorobenzaldehyde.

7. The process of claim 6 wherein the molar ratio of said pinacolone to said p-chlorobenzaldehyde is between about 1.5 moles of said pinacolone for each mole of said p-chlorobenzaldehyde to about 5 moles of said pinacolone for each mole of said p-chlorobenzaldehyde.

8. The process of claim 7 wherein the molar ratio of said pinacolone to said p-chlorobenzaldehyde is between about 1.75 moles of said pinacolone for each mote of said p-chlorobenzaldehyde to about 2.25 moles of said pinacolone for each mole of said p-chloro-benzaldehyde.

9. The process of claim 1 wherein said base is selected from alkali metal hydroxides, alkaline earth metal hydroxides, tetraalkylammonium hydroxides and combinations thereof.

10. The process of claim 9 wherein said base is added in a molar ratio of about 0.05 moles of said base for each mole of said p-chloro-benzaldehyde to about 5 moles of said base for each mole of said p-chlorobenzaldehyde.

11. The process of claim 10 wherein said base is added in a molar ratio of about 0.1 moles of said base for each mole of said p-chloro-benzaldehyde to about 1 mole of said base for each mole of said p-chlorobenzaldehyde.

12. The process of claim 11 wherein said base is added in a molar ratio of about 0.15 moles of said base for each mole of said p-chloro-benzaldehyde to about 0.25 moles of said base for each mole of said p-chlorobenzaldehyde.

13. The process of claim 9, 10, 11 or 12 wherein said base is sodium hydroxide.

14. The process of claim 1 wherein the initial concentration of said base in the aqueous phase of said reaction mixture is in the range of about 5% to about 80%.

15. The process of claim 14 wherein the initial concentration of said base in the aqueous phase of said reaction mixture is in the range of about 20% to about 50%.

16. The process of claim 15 wherein the initial concentration of said base in the aqueous phase of said reaction mixture is in the range of about 30% to about 40%.

17. The process of claim 1 wherein said phase transfer catalyst is selected from tetrasubstituted ammonium halides, tetrasubstituted phosphonium halides and combinations thereof.

18. The process of claim 17 wherein said phase transfer catalyst is selected from tetrabutylammonium bromide, methyltributylammonium chloride, benzyltriethylammonium chloride, tetrabutylammonium chloride and combinations thereof.

19. The process of claim 1 wherein said phase transfer catalyst is added in a molar ratio of about 0.0001 moles to 1.0 mole of said catalyst per mole of said p-chlorobenzaldehyde.

20. The process of claim 19 wherein said phase transfer catalyst is added in a molar ratio of about 0.001 moles to 0.1 moles of said catalyst per mole of said p-chlorobenzaldehyde.

21. The process of claim 2 wherein said neutralizing step comprises adding a neutralizing agent to said reaction mixture to bring the pH of said reaction mixture to a pH in the range of about 7 to about 10.

22. The process of claim 21 wherein said neutralizing agent is an acid.

23. The process of claim 22 wherein said acid is a mineral acid.

24. The process of claim 23 wherein said mineral acid is selected from hydrochloric acid, sulfuric acid, orthophosphoric acid and combinations thereof.

25. The process of claim 1 wherein said isolating step comprises:
    (a) separating said aqueous phase from said organic phase,
    (b) subjecting said organic phase to a distillation process to recover said pinacolone;
    (c) recovering said Phenyl aldol as the organic phase remaining after said distillation process.

26. The process of claim 1 wherein said Phenyl aldol is isolated and recovered in the absence of a filtration and/or a crystallization process.

27. A process for the production of Phenyl aldol comprising:
    (a) reacting p-chlorobenzaldehyde and pinacolone in the presence of a base and a phase transfer catalyst to form a reaction mixture comprising an organic phase and an aqueous phase, wherein said pinacolone may optionally be present in a stoichometric excess of the amount necessary to react with said p-chlorobenzaldehyde;

(b) optionally neutralizing said reaction mixture with an acid to a pH of about 7 to about 10;
(c) separating said aqueous phase from said organic phase,
(d) distilling said reaction mixture, wherein
   (i) if said distilling step is performed before said separating step, both said aqueous phase and said organic phase are subjected to a steam distillation process to recover any excess of said pinacolone;
   (ii) if said distilling step is performed after said separating step, said organic phase is subjected to a distillation process to remove any excess of said pinacolone; and
(e) recovering said Phenyl aldol as the organic phase remaining after said distillation process,
wherein said pinacolone is present in a mole ratio of about between about 0.5 moles of said pinacolone for each mole of said p-chlorobenzaldehyde to about 10 moles of said pinacolone for each mole of said p-chlorobenzaldehyde,
wherein said base is present in a molar ratio of about 0.05 moles of said base for each mole of said p-chlorobenzaldehyde to about 5 moles of said base for each mole of said p-chlorobenzaldehyde,
wherein said phase transfer catalyst is present in a molar ratio of about 0.0001 moles to 1.0 mole of said catalyst per mole of said p-chlorobenzaldehyde,
wherein said reacting step occurs in the temperature range between about 0° C. and the reflux temperature of said reaction mixture.

28. The process of claim 27, wherein said base is sodium hydroxide, said phase transfer catalyst is selected from tetrabutylammonium bromide, methyltributylammonium chloride, benzyltriethylammonium chloride, tetrabutylammonium chloride and combinations thereof, and said acid is selected from hydrochloric acid, sulfuric acid, orthophosphoric acid and combinations thereof.

29. The process of claim 28 wherein said Phenyl aldol is formed without the addition of an organic solvent and is recovered without crystallization or filtration steps.

* * * * *